United States Patent [19]

Plaitakis

[11] Patent Number: 5,028,622

[45] Date of Patent: Jul. 2, 1991

[54] ADMINISTRATION OF AMINO ACIDS AS TREATMENT FOR NEURODEGENERATIVE DISORDERS

[75] Inventor: Andreas Plaitakis, New Rochelle, N.Y.

[73] Assignee: Ajinomoto Company, Inc., Tokyo, Japan

[21] Appl. No.: 363,351

[22] Filed: Jun. 6, 1989

Related U.S. Application Data

[63] Continuation of Ser. No. 190,765, May 6, 1988, abandoned.

[51] Int. Cl.[5] ............................................. A61K 31/195
[52] U.S. Cl. ..................................................... 514/561
[58] Field of Search ........................................ 514/561

[56] References Cited

U.S. PATENT DOCUMENTS 4,438,144  3/1984  Blackburn ........................... 514/561

OTHER PUBLICATIONS

A. Plaitakis and J. T. Caroscio, "Abnormal Glutmate Metabolism in Amyotrophic Lateral Sclerosis", *Ann. Neurol.*, 22, pp. 575-579 (1987).

R. Tandan and W. G. Bradley, "Amyotrophic Lateral Sclerosis: Part 2, Etiopathogenesis", Ann. Neurol. 18, pp. 419-431 (1985).

P. S. Spencer et al., "Guam Amyotrophic Lateral Sclerosis-Parkinsonism-Dementia Linked to a Plant Excitant Neurotoxin", *Science*, 237, pp. 517-522 (1987).

A. Plaitakis et al., "Neurological Disorders Associated with Deficiency of Glutamate Dehydrogenase", *Ann. Neurol.* 15, pp. 144-153 (1984).

A. Plaitakis et al., "Abnormal Glutamate Metabolism in an Adult-Onset Degenerative Neurological Disorder", *Science*, 216, pp. 193-196 (1982).

A. Plaitakis et al., "The Treatment of GDH-Deficient Olivopantocerebellar Atrophy with Branched Chain Amino Acids", Neurology, 33 (Suppl. 2), p. 78 (1983).

J. W. Olney et al., "Cytotoxic Effects of Acidic and Sulphur Containing Amino Acids on the Infant Mouse Central Nervous System", *Exp. Brain Res.*, 14, pp. 61-76 (1971).

R. Schwarcz et al., "Current Topics, II Excitotoxic Models for Neurodegenerative Disorders", *Life Sciences*, 35, pp. 19-32 (1984).

B. Engelsen, "Neurotransmitter Glutamate: Its Clinical Importance", *Acta Neurol. Scand.* 74, pp. 337-355 (1986).

S. S. Stewart and S. H. Appel, "The Treatment of Amyotrophic Lateral Sclerosis", in *Current Neurology Yearbook Publishers, Inc.*, 7, pp. 51-90 (1987).

S. M. Ross et al., "Specific Antagonism of Excitotoxic Action of Uncommon Amino Acids Assayed in Organotypic Mouse Cortical Cultures", *Brain Research*, 425, pp. 120-127 (1987).

K. L. Yielding and G. M. Tomkins, "An Effect of L-Leucine and Other Essential Amino Acids on the Structure and Activity of Glutamic Dehydrogenase", *Proc. Natl. Acad. Sci. USA*, 47, 983-989 (1961).

(List continued on next page.)

*Primary Examiner*—Stanley J. Friedman
*Attorney, Agent, or Firm*—Oblon, Spivak, McClelland, Maier & Neustadt

[57] ABSTRACT

A treatment and composition for preventing in mammals the progressive exacerbation of symptoms associated with neurodegenerative disorders characterized by abnormal glutamate metabolism, elevated levels of peripheral glutamate or altered glutamate receptor characteristics. The treatment is comprised of the administration of compositions comprised of amino acids that are effective in retarding the development of symptoms associated with neurodegenerative disorders, presumably by activating the enzyme glutamate dehydrogenase. In the preferred embodiment, the branched chain amino acids L-leucine, L-isoleucine, and L-valine are disclosed as effective therapeutic agents for the treatment of amyotrophic lateral sclerosis.

24 Claims, 4 Drawing Sheets

OTHER PUBLICATIONS

A. Senner and W. J. Malaisse, "The Stimulus–Secretion Coupling of Amino Acid-Induced Insulin Release. Insulinotropic Action of Branched Chain Amino Acids at Physiological Concentrations of Glucose and Glutamine", *European J. of Clin. Invest*, 11, pp. 455–460 (1981).

A. Senner et al., "The Stimulus–Secretion Coupling of Amino Acid-Induced Insulin Release XI. Kinetics of Deamination and Transamination Reactions", *Horm. Metabol. Res.*, 14, pp. 405–409 (1982).

T. I. Rao et al., "Studies on Metabolism of Branched Chain Amino Acids in Brain and Other Tissues of Rat With Special Reference to Leucine", *J. of Neurosci. Res.* 7, pp. 387–395 (1982).

J. E. Fischer et al., "Plasma Amino Acids in Patients with Hepatic Encephalopathy: Effects of Amino Acid Infusions", *Amer. J. of Surg.*, 127, pp. 40–47 (1974).

Rote Liste, No. 56 086, Edito Cantor, Aulendorf/Wurtt; *Lactostrict Spezial Unlisted Drugs*, vol. 37, No. 5, May 1985, Chatham, New Jersey, U.S.; "Illevasorb".

V, Iob et al., "Altered Clearance of Free Amino Acids from Plasma of Patients with Cirrhosis of the Liver", *J. of Surg. Res.*, 6, pp. 233–239 (1966).

B. M. Patten and L. M. Klein, "L-Threonine and the Modification of ALS", Neurology, 35 (Suppl 1), p. 354 (1988).

R. Schwarcz and B. Meldrum, "Excitatory Aminoacid Antagonists Provide a Therapeutic Approach to Neurological Disorders", *Lancet*, 8447, pp. 140–143 (1985).

ADMINISTRATION OF AMINO ACIDS AS TREATMENT FOR NEURODEGENERATIVE DISORDERS

This is a continuation, of application Ser. No. 190,765, filed May 6, 1988, now abandoned, entitled ADMINISTRATION OF AMINO ACIDS AS TREATMENT FOR NEURODEGENERATIVE DISORDERS.

TECHNICAL FIELD OF THE INVENTION

This invention relates to treatments and compositions useful for preventing the exacerbation of symptoms associated with neurodegenerative disorders in mammals. Specifically, compositions which are comprised of branched chain amino acids, such as L-leucine, L-isoleucine, and L-valine and which activate the enzyme glutamate dehydrogenase are disclosed. This invention also relates to protocols for their use, which are efficacious for retarding the progression of symptoms associated with neurodegenerative disorders such as amyotrophic lateral sclerosis (ALS). The treatments and compositions disclosed have application for the treatment of neurodegenerative disorders characterized either by altered metabolism of glutamate, increased levels of peripheral glutamate, or altered glutamate receptor characteristics. The treatments and compositions disclosed presumably provide protection against the excitotoxic actions of glutamate.

BACKGROUND OF THE INVENTION

The neurotoxicity of excitatory neurotransmitters has led to the development of the excitotoxicity hypothesis for neuronal cell death. [For review see, B. Engelsen, "Neurotransmitter Glutamate: its Clinical Importance", *Acta Neurol Scand,* 1986, 74:337-355; R. Schwarcz and B. Meldrum, "Excitatory Aminoacid Antagonists Provide a Therapeutic Approach to Neurologic Disorders", *Lancet,* 1985, 8447: 140-143] According to this hypothesis, sustained depolarization of neurons expressing receptors for excitatory amino acids ultimately leads to irreversible damage and their death. Sustained depolarizations may arise from several different mechanisms including increased release of glutamate, decreased reuptake of glutamate, or alterations in the characteristics of the glutamate receptor. The presence of one or more of these mechanisms in an individual may result in neurodegeneration and the onset of clinical symptons. Several neurodegenerative disorders have been identified which are associated with one or more of the above alterations of glutamate activity. [B. Engelsen, "Neurotransmitter Glutamate: its Clinical Importance", *Acta Neurol Scand,* 1986, 74:337-355. The contents of this reference are herein incorporated by reference].

As toxicity has been associated with sustained depolarization through receptor activation, the predominant approach towards preventing the neurotoxic effect of neuroexcitatory neurotransmitters has been to develop effective antagonists for neuroexcitatory receptors. [R. Schwarcz and B. Meldrum, "Excitatory Aminoacid Antagonists Provide a Therapeutic Approach to Neurologic Disorders," *Lancet,* 1985, 8447: 140-143; S. M. Ross, M. Seelig, and P. Spencer, "Specific Antagonism of Excitotoxic action of 'Uncommon' amino acids in Organotypic Mouse Cortical cultures," *Brain Res.,* 1987, 425:120-127] An example of this approach is the study of Guam ALS. The neurotoxic acitivity of beta-N-Methylamino-L-alanin (BMAA) and beta-N-oxalylamino-L-alanine (BOAA), compounds which are present in seeds of *Cycas circinalis* and *Lathyrus sativus,* respectively and which have been implicated in the eitology of Guam ALS, have been selectively antagonized in a concentration dependent manner by compounds which are specific antagonists of glutamate receptor sites. Thus, the development of specifically designed antagonists, especially those which block NMDA glutamate receptors, has been suggested to be "[o]ne of the most promising concepts concerning a rational treatment of neurodegenerative disorders[.]" [R. Schwarcz and B. Meldrum, "Excitatory Aminoacid Antagonists Provide a Therapeutic Approach to Neurologic Disorders, *Lancet,* 1985, 8447: 140-143 ]

Amyotrophic lateral sclerosis is a relentlessly progressive neurological disorder that is manifested primarily by muscle weakness, wasting, and spasticity, usually resulting in death from debilitating disease in 2-5 years [Brain, The Lord, Croft P., Wilkinson M. The course and outcome of motor neuron disease. In: Norris FH, Jurland LT, eds. *Motor Neuron Diseases.* New York: Grune and Stratton, 1967:22]. No treatment is known at present that can influence the course of the disease.

The cause of ALS is unknown. Recent studies [Plaitakis A., Carosoio JT. "Abnormal glutamate metabolism in amyotrophic lateral sclerosis," *Ann Neurol* 1987. 22:575-579], however, have shown that the metabolism of the neuroexcitotoxic amino acid glutamate [Olney JW. "Neurotoxicity of excitatory amino acids," In: McGeer EG, Olney JW, McGeer PL eds. Kainic Acid as a Tool in *Neurobiology.* New York: Raven Press, 1978:95-121] is altered in this disorder and that the possibility exists that neurodegenerative processes in ALS may be mediated by neuroexcitotoxic mechanisms [Plaitakis A., Caroscio JT. "Abnormal glutamate metabolism in amyotrophic lateral sclerosis," *Ann Neurol* 1987. 22:575-579; Spencer PS, Nunn PB, Hugon J. et al. "Guam amyotrophic lateral sclerosis-Parkinsonism-dementia linked to a plant excitant neurotoxin," *Science,* 1987, 237:517-522].

Abnormal glutamate metabolism has, in addition to ALS, been shown to occur in patients with late-onset multi-system atrophic disorders associated with decreased activity of the enzyme glutamate dehydrogenase (GDH). [Plaitakis A., Berl S., Yahr MD. "Abnormal glutamate metabolism in an adult-onset neurological disorder," *Science,* 1982, 216:193-196]. Some of these patients with decreased GDH activity have been described to show predominant motor neuron involvement, or atypical ALS. [Plaitakis A., Berl S., Yahr MD. "Neurological disorders associated with deficiency of glutamate dehydrogenase," *Ann. Neurol.* 1984, 15:144-153]. GDH is particularly important in the biology of the nervous system and the integrity of motor neurons. GDH can be activated by the branched chain amino acids (BCAA) L-leucine and L-isoleucine [Yielding KL, Tomkins GM. "An effect of L-leucine and other essential amino acids on the structure and activity of glutamate dehydrogenase," *Proc. Natl. Acad. Sci. USA,* 1961, 47:983].

This invention relates to the use of dietary supplementation with branched chain amino acids (BCAAs) L-leucine, L-isoleucine and L-valine to benefit patients with idiopathic ALS. These compounds have been shown to allosterically activate, in vitro, glutamate dehydrogenase [Yielding KL, Tomkins GM. "An Effect of L-leucine and other essential amino acids on the structure and activity of glutamate dehydrogenase," *Proc. Natl. Acad. Sci. USA*, 1961, 47:983] and modify the metabolism of glutamate [Dennis S., Clark, J. B. "The synthesis of glutamate by rat brain mitochondria," *J. Neurochem* 1986; 46:1811–1819], which is reported to be altered in ALS [Plaitakis A., Caroscio J. T. "Abnormal glutamate metabolism in amyotrophic lateral sclerosis," *Ann Neurol* 1987. 22:575–579].

Evidence of the novelty of the treatments and compositions disclosed by this invention is indicated by a recent report which describes the use of L-threonine to modify the progression of ALS. [B. M. Patten and L. M. Klein, "L-Threonine and the Modification of ALS," *Neurology*, 1988, 38 (Suppl 1):354–355] To substitute for L-threonine, L-leucine or L-isoleucine were used as placebos. Patients treated with placebo were reported to "revert to previous status.".

SUMMARY OF THE INVENTION

This invention relates to a novel treatment for neurodegenerative disorders. The compositions of this invention prevent the progression of symptoms associated with neurodegenerative disorders. The preferred compositions are comprised of branched chain amino acids (BCAA) which may be administered to patients in therapeutically effective amounts.

Twenty-two patients with amyotrophic lateral sclerosis (ALS) were entered into a double-blind, randomized, placebo-controlled trial to test whether the administration of branched-chain amino acids could favorably influence the course of the disease. Eleven patients received daily 12 grams of L-leucine, 8 grams of L-isoleucine and 6.4 grams of L-valine, given orally, and the remainder received placebo.

During the one-year trial, the placebo-treated patients showed a linear decline in their functional status consistent with the natural history of the disease. In contrast, the amino acid-treated patients showed a substantial stabilization of their neurologic status with significantly better maintenance of extremity muscle strength and continued ability to remain ambulatory than those treated with placebo.

Symbols refer to comparisons between the placebo and the amino acid treated group at each time point (using the unpaired t test). * Denotes $p<0.02$., † $p<0.05$ and $\ddagger p<0.1$ of placebo compared to treated group.

Figure 1A:
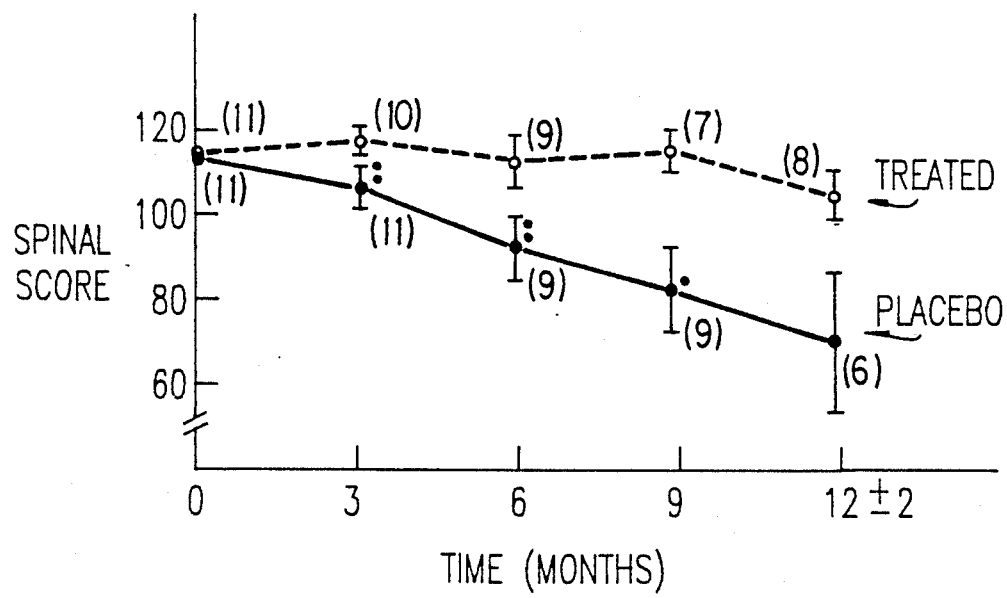
FIG. 1A. Mean Spinal Scores in the Branched-Chain Amino Acid (Treated) and Placebo Groups. (N) is the number of patients who were clinically assessed at each time point as described in the Methods. The (N) decreased during the progress of the trial due to 1) death from the disease or severe disability precluding a visit to the clinic, 2) withdrawal from the study and 3) occasionally, non-compliance with the clinic appointments (Table 3). Two amino acid treated patients who could not attend the clinic at 12 months were instead evaluated at the 14th month of the trial. Values are means for each group ±SEM.
Figure 1B:
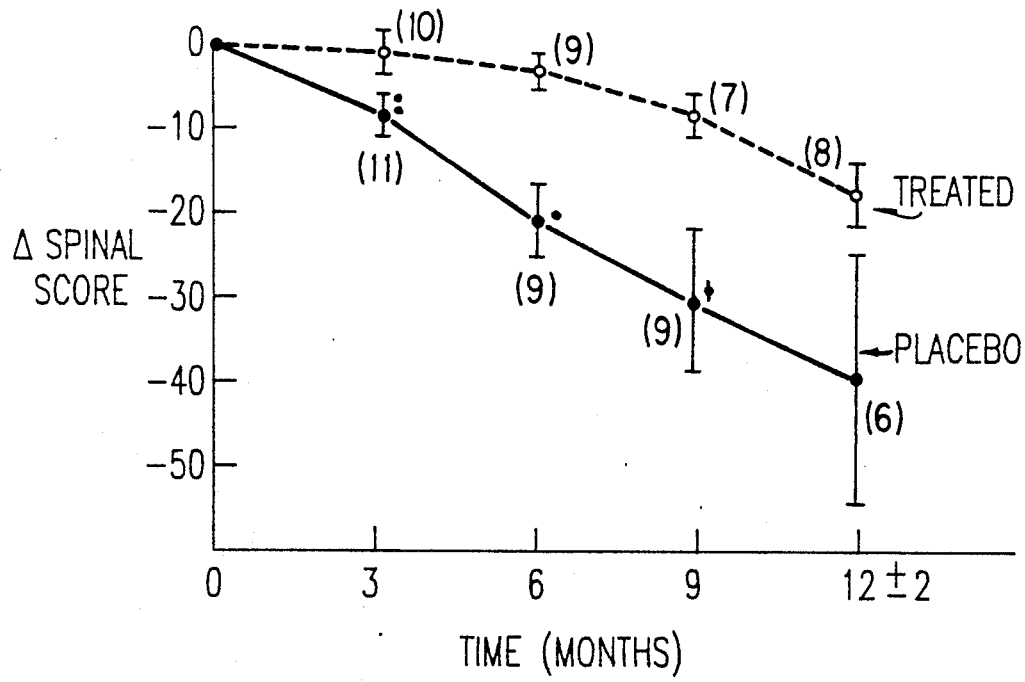

FIG. 1B. Comparison of spinal score differences from baseline (Δspinal score) for placebo and amino acid-treated (treated) groups. The difference was calculated by subtracting the baseline value from the value at each time pont for each subject. Values are means ±SEM. For explanation of symbols set FIG. 1A.

Figure 2:
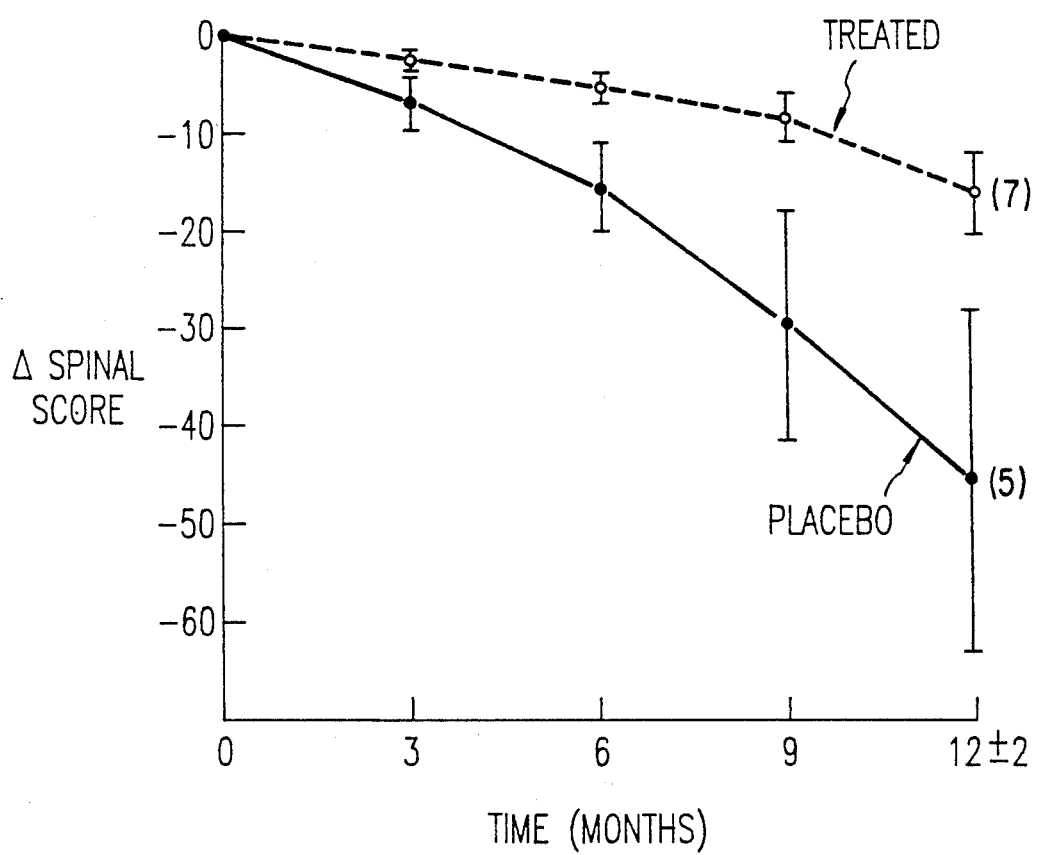

FIG. 2. Comparisons of the spinal score differences from baseline for only those amino acid-treated (treated) and placebo-treated (placebo) patients who had complete observations for 12 months. Repeated measures analysis of variance showed that the time by group interaction was significant at $p=0.033$ ($F=3.33$) level.

Figure 3:
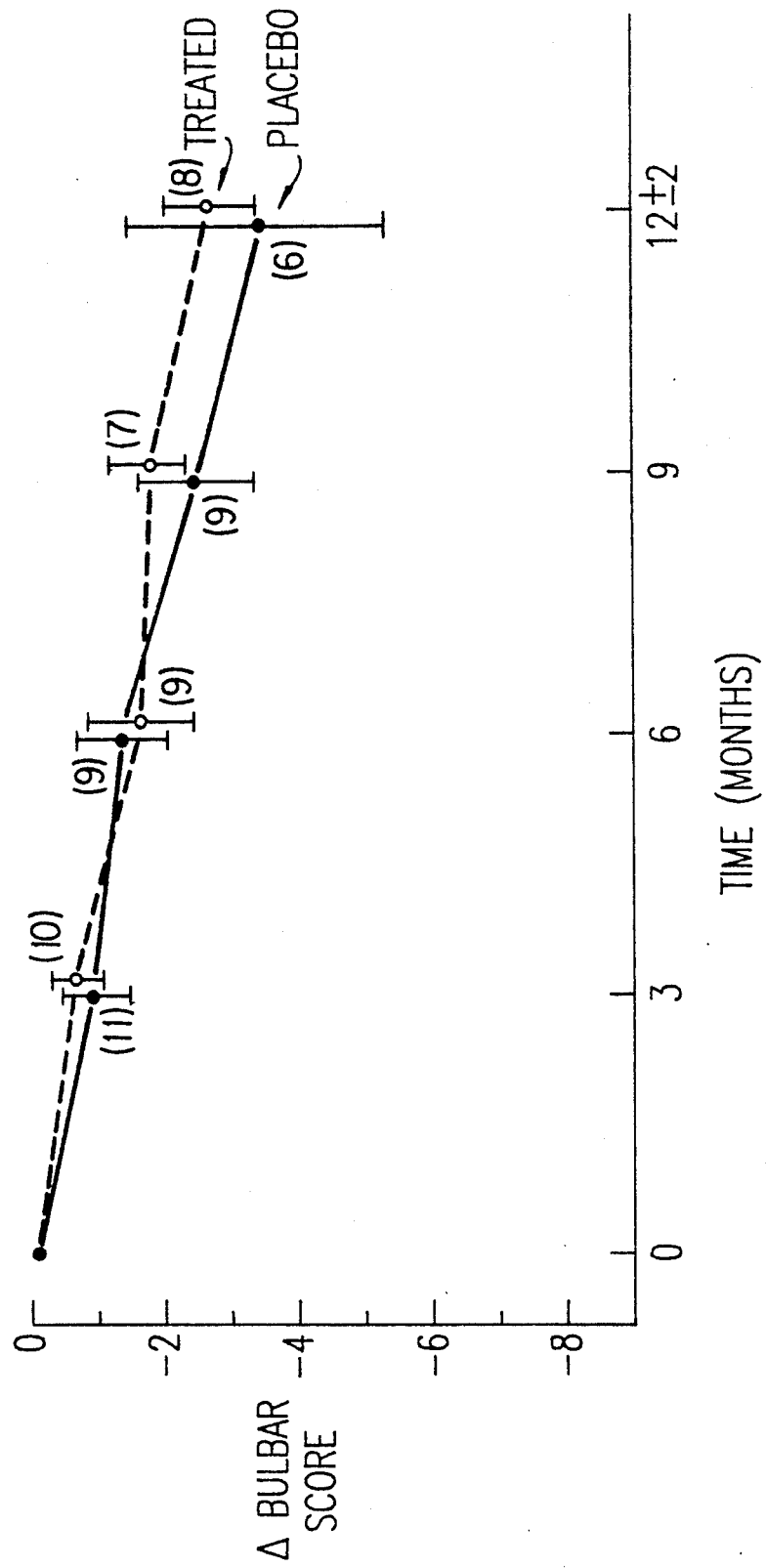

FIG. 3. Changes in Bulbar Scores for the Amino Acid (treated) and Placebo Groups. Bulbar function was clinically assessed at each time point as described in the methods. Values are means for each group ±SEM and represent differences from baseline values (Δbulbar score) as described in FIG. 1B.

Figure 4:
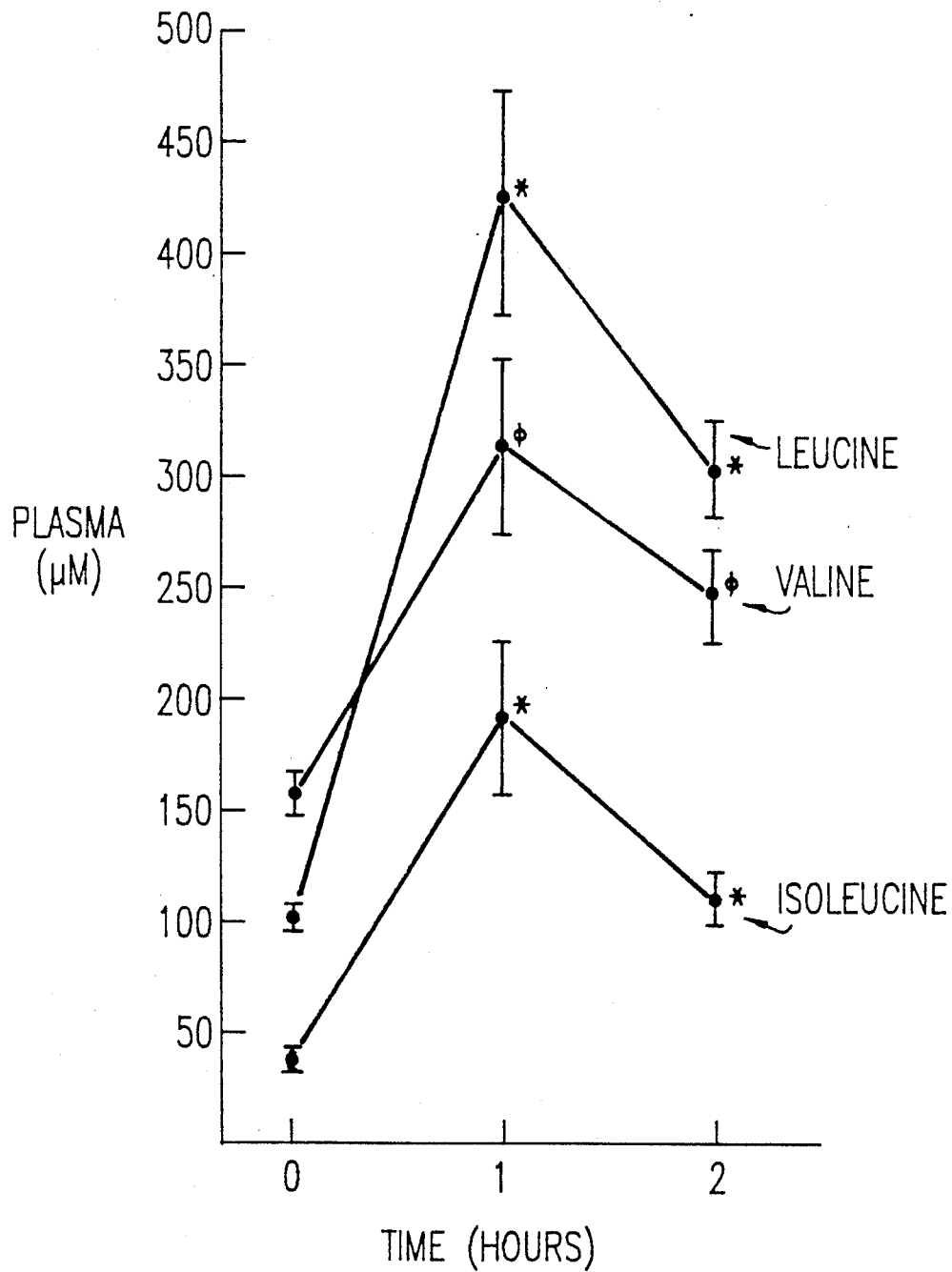

FIG. 4. Results of the branched-chain amino acid oral test dose. After overnight fasting, the ALS patients randomized to treatment received orally 3.0 grams of L-leucine, 2.0 grams of L-isoleucine and 1.6 grams of L-valine mixed thoroughly in dietetic jello. Blood samples were drawn at the times indicated and processed as previously described(5). Data points represent mean values from 9 patients ±SEM. * Denotes $p<0.001$ and † $p<005$. Symbols refer comparisons to 0 time values according to the student's t-test.

DETAILED DESCRIPTION OF THE INVENTION

In accordance with the subject of this invention a treatment is disclosed which is efficacious for preventing the progressive exacerbation of symptoms associated with neurodegenerative disorders characterized by abnormal glutamate metabolism, elevated levels of peripheral glutamate, or altered glutamate receptor characteristics. The treatment is comprised of administering to individuals in need of treatment a mixture of amino acids which activate the enzyme glutamate dehydrogenase.

Glutamate has been implicated in the pathogenesis of several human neurodegenerative disorders. Various human neurodegenerative disorders have been associated with one or more alterations involving glutamate including altered metabolism of glutamate, increased peripheral levels of glutamate, or altered glutamate receptor characteristics.

Glutamate, is an excitatory neurotransmitter which is also toxic to neurons. The neurotoxic activity of several excitatory neurotransmitters has led to the development of "excitotoxic models for human diseases." [R. Schwarcz and B. Meldrum. "Excitatory Aminoacid Antagonists Provide a Therapeutic Approach to Neurological Disorder," *Lancet*, July 20, 10 1985, 140–143. The contents of which are herein incorporated by reference] GDH catalyzes the conversion of glutamate to alpha-ketoglutarate. The disclosed invention provides treatments and compositions which presumably increase the endogenous activity of GDH thereby increasing the catabolism of glutamate as well as modifying the glutamatergic transmission mechanisms in the CNS to decrease its toxic activity. This is a completey novel approach to the treatment of neurodegenerative disorders. Most other approaches to the treatment of neurodegenerative disorders arising from excitotoxic mechanisms have focused on the use of receptor antagonists to inhibit the action of excitatory neurotransmitters such as glutamate.

Thus, this invention relates to the treatment of disorders that have been associated with glutamate toxicity. Such disorders include, but are not limited to amyotrophic lateral sclerois, Alzheimer's disease, Huntington's disease, spinocerebellar degenerations, and other disorders characterized by degeneration of motor and other neurons of the central nervous system. This invention may have application as well and be useful for the treatment of other types of neurological disorders in which glutamate may be involved, such as seizure disorders, ischemic brain injury, or stroke, multiple sclerosis, and AIDS. This invention may have veterinary application as well.

The treatment comprises the administration of a therapeutically effective amount of a composition comprised of one or more amino acids. Amino acids which activate glutamate dehydrogenase or are effective, either alone or in combination with other amino acids, for the treatment of one or more neurodegenerative disorders are appropriate ingredients of the composition. Such compositions may be comprised of branched chain amino acids. A preferred composition is comprised of L-leucine, L-isoleucine, and L-valine. The preferred composition has particular application to the treatment of amyotrophic lateral sclerosis (ALS).

Treatments using the compositions provided for by this invention should be administered so as to maintain minimum effective therapeutic concentrations of the composition constituents in plasma and other appropriate tissues. A preferred composition is comprised of L-leucine, L-isoleucine and L-valine, wherein the ratio of the amounts of L-leucine: L-isoleucine:L-valine present in the composition range from 0.3–30:0.2–20:0.16–16. The preferred range for the ratio of the amount of L-leucine:L-isoleucine: L-valine present in the composition is 3.0:2.0:1.6. For the treatment of neurodegenerative disorders, and particularly ALS, the amino acid composition should provide a total daily dose per individual of about 0.3 to 30 grams of L-leucine, 0.2 to 20 grams of L-isoleucine, and 0.16 to 16 grams L-valine. The preferred ranges of the total daily dose of each of the amino acids of the composition are about: 12 to 18 grams of L-leucine, 8 to 12 grams of L-isoleucine, and 3.2 to 9.6 grams of L-valine. The total daily dose may be divided so as to be administered using a variety of different protocols. Preferred protocols provide for the administration of the composition four or six times per day in amounts such that the total amount of composition administered per day is equal to the total daily dose. Administration of the composition may either be orally or parenterally.

Plasma levels of the amino acids of the composition may be monitored to assess whether effective levels are being maintained. The treatment disclosed by this invention provides for doses of amino acids in amounts sufficient to increase plasma levels above untreated levels. The ranges of the percent increase over untreated levels for each of the amino acids are about 50 to 600 % for L-leucine; 40 to 500 % for L-isoleucine; and 25 to 300 % for L-valine. The preferred ranges for the percent increase in plasma levels over untreated levels are about 100 to 300 % for L-leucine, 80 to 250 % for L-isoleucine, and 50 to 150 % for L-valine.

EXAMPLE 1

Patients and Methods

Patients

Twenty-two patients were studied. The criteria for entry included (1) unequivocal diagnosis of ALS after a complete clinical investigation and EMG confirmation, (2) a stage of disease in which all patients were ambulatory at the time of entry, (3) normal biochemical and hematological profile and (4) lack of evidence for a systemic disease.

The patients were entered into the study sequentially as seen in the Mt. Sinai Hospital, New York, ALS clinic and randomly assigned to receive either BCAA powder or a similar amount of placebo powder (starch), with care taken to have equal numbers of subjects in both study groups. The BCAA powder consisted of 3.0 grams of L-leucine, 2.0 grams L-isoleucine and 1.6 grams of L-valine. Patients were instructed to take this orally four times daily between meals throughout the entire twelve month study period.

Each patient was then seen at three-month intervals for the clinical and laboratory assessments described below. The family, the patient, the nursing staff and the neurologists who performed the clinical evaluation were blinded as to the medication being used. The trial was terminated and the code was broken after all patients had completed twelve months on treatment.

Administration of L-leucine alone has been found to severely depress the plasma and CSF levels of the other two BCAAs; however, when given in tandem with them, it produces significant increases in blood and CSF levels of all three compounds [Plaitakis A., Berl S., Yahr MD. "The treatment of GDH-deficient olivopontocerebellar atrophy with branched chain amino acids," *Neurology* 1983;33:(suppl 2):78 which is hereby incorporated by reference].

Neurologic Evaluation

Objective neurologic ratings of patient's status were performed [Caroscio JT, Cohen JA, Zawodniak J. et al., "A double-blind placebo-controlled trial of TRH in amyotrophic lateral sclerosis," *Neurology* 1986; 36:141–145 which is hereby incorporated by reference], including a spinal score and a bulbar score. The spinal score was the sum of muscle power rates obtained by manual testing of 13 muscle groups on left and right as described in the Table 1. For the bulbar score speech articulation, reported ability to swallow food and facial, tongue and palatal movements were each semi-quantitated as also described in Table 1. Bulbar and spinal scores were obtained and recorded on a standard collection sheet which was pat of the patient's chart. Ability to ambulate was also observed (untimed) and descriptively recorded. Most ratings were performed by the same examiner in individual patients; this method of clinical assessment has been shown to be reproducible. [Caroscio JT, Cohen JA, Zawodniak J. et al., "A double-blind placebo-controlled trial of TRH in amyotrophic lateral sclerosis, " *Neurology* 1986; 36:141–145 which is hereby incorporated by reference]

TABLE 1

| Method of Estimating Bulbar and Spinal Scores |
|---|
| (a) Bulbar score:<br>    Normal = 3<br>    Mild impairment = 2<br>    Moderate impairment = 1<br>    Marked impairment = 0<br>    Evaluation by this scale was made for<br>    the following bulbar functions:<br>    (1) facial movement<br>    (2) tongue movement<br>    (3) palatal movement<br>    (4) dysarthria<br>    (5) dysphagia<br>    Maximum score = 15 (All bulbar<br>    functions were weighted equally)<br>(b) Spinal score |

TABLE 1-continued
Method of Estimating Bulbar and Spinal Scores

A power rating for individual muscle groups was obtained by the following scale;
- 5 = normal strength
- 4.5 = able to overcome marked resistance
- 4 = able to overcome moderate resistance
- 3.5 = able to overcome mild resistance
- 3 = able to overcome gravity but not resistance
- 2 = able to contract muscle with gravity eliminated
- 1 = flicker of movement
- 0 = no movement Evaluation by this scale was made for the following paired (right and left) muscle groups:
- (1) arm abduction
- (2) elbow flexion
- (3) elbow extension
- (4) wrist flexion
- (5) wrist extension
- (6) finger flexion
- (7) finger extension
- (8) finger abduction
- (9) hip flexion
- (10) knee flexion
- (11) knee extension
- (12) foot dorsiflexion
- (13) foot plantar flexion Maximum score = 130 (All muscle groups were weighted equally)

Laboratory Studies

Baseline blood chemistries and complete blood counts (CBC were obtained. To assure bioavailability of the BCAA, an oral test dose of the above-described mixture or placebo was given after overnight fasting at baseline. Blood samples were drawn at 0, 60 and 120 minutes after dosing for multi-chemistries, CBSs and serum ammonia and amino acid levels. In addition, a random blood sample was obtained for the above studies at three month intervals with no attention paid to time of oral dosing. Plasma amino acid levels were assayed as previously described. [A. Platakis and J. Caroscio, "Abnormal Glutamate Metabolism in Amyotrophic Lateral Sclerosis," *Ann Neurol,* 1987, 22:575-579. The contents of this article are herein incorporated by reference]

Statistical Analysis

Mean clinical scores for the two groups were calculated for values at baseline and at each three-month interval and were compared using the unpaired t-test. In addition the differences between the baseline and the scores obtained in each three month interval were statistically compared for the two groups using again the unpaired t-test. All t-tests were two sided.

Repeated measures analysis of variance was calculated on the clinical scores for the time periods 0, 3, 6, 9, and 12 months for all patients having complete data. The same analysis was also done for the time periods 0, 3, 6, and 9 months only, as well as for 0, 3, and 6 months only.

The outcome of the study was evaluated using two criteria: (1) rate of decline in scores of each group and (2) continued ability to remain ambulatory at termination of the study. The proportion of success of the second criterion in each of the two groups was statistically compared using the chi-squared statistic and Fisher's exact test. Included in this analysis were all patients who completed the trial as well as those who, while under treatment, progressed to the point of wheelchair confinement (classified as failures) but did not complete one year on the trial either due to death or subsequent withdrawal. Patients who withdrew while still ambulatory were excluded from analysis because they could not be classified as successes without having completed 12 months of observation.

Results

Twenty-two patients meeting the requirements for entry were included in the study. Eleven patients were assigned to BCAA treatment, the remainder to placebo. An additional patient assigned to BCAA was lost to follow-up within a month and was not included in any of the analyses. The clinical characteristics of the two treatment groups did not differ significantly (Table 2).

TABLE 2
Clinical Characteristics of ALS Patients at Entry into the Study, According to Treatment Group

| Characteristics | Branched-chain Amino-Acids | Placebo |
|---|---|---|
| Male | 10 | 9 |
| Female | 1 | 2 |
| Disease Duration | | |
| <2 years | 7 | 6 |
| >2 years | 4 | 5 |
| Mean Disease Duration (years) | 1.8 ± 2.0* | 1.9 ± 1.2* |
| Mean Age (years) | 48.5 ± 11.9* | 53.7 ± 11.5* |
| Mean Spinal Score (Normal = 130) | 115.9 ± 15.6* | 114.7 ± 11.1* |
| Mean Bulbar Score (Normal = 15) | 12.5 ± 2.2* | 13.2 ± 2.2* |

*Values are means ± S.D.

Table 3 shows the number of patients who remained on the protocol throughout the trial, as well as those who withdrew, become respirator-dependent or died of their disease.

TABLE 3
Number Of ALS Patients On And Off Protocol During The Trial

| | Amino Acid Treated | | Placebo Treated | |
|---|---|---|---|---|
| Time on the Trial | On Protocol | Off Protocol | On Protocol | Off Protocol |
| 0 | 11 | 0 | 11 | 0 |
| 3 months | 11* | 0 | 11 | 0 |
| 6 months | 10* | 1 (withdrawal) | 10* | 1 (withdrawal) |
| 9 months | 8* | 2 (withdrawals) | 9 | 1 (death) |
| 12 ± 2 months | 8 | 0 | 6 | 3 (death: 1 withdrawal: 1 respirator: 1) |

*One patient was unable to attend clinic for evaluation at this time but remained on treatment and was evaluated on subsequent visits.

FIG. 1A shows the mean spinal scores obtained in all patients in each group at three-month intervals and FIG. 1B shows the changes in these scores (values at the time points minus baseline values). FIG. 2 shows changes in spiral scores of only those patients who had complete observations for 12 months. THe changes were significantly worse in the placebo-treated patients than in the BCAA-treated patients.

Repeated measures analysis of the spinal scores for all patients who completed the trial revealed significant differences in the rate of progression of the disease between the two groups. Thus, a statistically significant time X group interaction was found for the time periods: (a) 0-6 months (F=7.13, p=0.0003) (N=17, drug group=9, placebo group=8) and (b) 0-9 months (F=5.17, p=0.0004, N=15, drug group=7, placebo group=8) and (c) 0-12 months (F=3.6, p=0.013) (N=12, drug group=7, placebo group=5).

Due to progressve decline, five of the nine placebo-treated patients lost their ambulation during the trial with two subsequently dying and another becoming respirator-dependent (Table 3). In contrast, only one of the nine BCAA-treated subjects lost ambulation during observation (p<0.05 by the ohi square; p=0.066 by the Fisher's exact test). Two patients in each group who withdrew (Table 3) while still ambulatory were not included in this analysis (see Methods).

In contrast to the spinal scores, the changes in the bulbar scores were not significantly different between the two treated groups (FIG. 3). Also, there was no significant time X group interaction with respect to the bulbar scores. However, there was a significant change in the bulbar scores overall for baseline vs. nine months (p=0.025, F=6.79) and baseline vs. 12 months (p=0.016, F=8.16).

Plasma levels of leucine, isoleucine and valine showed marked increases following oral dosing (FIG. 4). Levels of leucine increased by 300% and 192%, of isoleucine by 393% and 183% and of valine by 95% and 53% after 1 and 2 hours, respectively. Routine blood chemistries and complete blood counts did not show any abnormalities following these oral loadings, except for mild transient elevations in the plasma ammonia levels (data not shown). Analysis of blood samples obtained randomly a various intervals during the one-year trial revealed that the amino acid-treated patients maintained plasma levels of BCAA that were significantly higher than those of the placebo-treated patients (leucine by 112%, isoleucine by 93% and valine by 61%). Also, complete blood counts and blood chemistries (including ammonia levels) did not show significant changes in the patients who were treated chronically with the BCAA.

Long-term controlled trials have proven difficult to perform in ALS [Shafter SR, Olarte MR. "Methodological considerations for clinical trials in motor neuron disease," In: Rowland P ed. *Human Motor Neuron Diseases*, New York, Raven Press, 1982, pp. 559-568] because of the high rate of patient loss (due to death or discontinuation of treatment) which complicates the analysis and interpretation of the data. An attrition rate of study patients as high as 70% has been described in one-year, double-blind, controlled trials [Olarte MR, Shafter SR. "Levamisole is ineffective in the treatment of amyotrophic lateral sclerosis," Neurology] 35:1063-1066].

Although some cases were lost during this study, the majority of treated patients completed the one-year trial. Analysis of the spinal scores, using all available measurements of every patient who was included in the trial, as well as the measurements of only those patients who had complete observations, revealed significant differences in the rate of progression between the two groups, regardless of the inclusion or exclusion of the patients who did not have complete data or did not complete the one-year trial.

Thus, the deterioration in the mean spinal performance scores for the BCAA-treated patients was 4% and 9% of the initial scores for 6 and 12 months respectively. In contrast, in the placebo group, deterioration of these scores was 18% and 38% for 6 and 12 months respectively. The decline in motor performance of our placebo-group was comparable to that described by Olarte et al. [Olarte MR, Shafter SR. "Levamisole is ineffective in the treatment of amyotrophic lateral sclerosis," *Neurology*, 1985, 35:1063-1066], who found a 15-25% and 20-30% decline in mean score for 6 and 12 months respectively, although direct comparisons are confounded by different scoring methods. Also, the death rate in the placebo group (2 out of 11 or 18.2%) was comparable to that in the study by Olarte et al. [Olarte MR, Shafter SR. "Levamisole is ineffective in the treatment of amyotrophic lateral sclerosis," *Neurology*, 1985, 35:1063-1066] (18.5% and 20.5% for their two groups).

The favorable results of this invention are clearly not due to difference in the severity of illness and approximate duration of illness prior to treatment in the two groups studied, which were rather well-matched. Because of the small sample size and because there is a substantial variation in the natural history of the disorder modifications of the treatment produced are likely to be developed based on the principle disclosed in this invention. Of some concern is the fact that no significant differences in the bulbar scores of the two groups were found. It should, however, be noted that clinical rating of bulbar motor function is less sensitive than spinal rating and that bulbar dysfunction tends to progress slower than spinal weakness in ALS patients.

This preliminary trial establishes a basis for a new therapeutic approach to ALS, and other disorders characterized by altered glutamate metabolism.

EXAMPLE 2

The ability of L-leucine to activate, in vitro, GDH present in post mortem brain tissue obtained from control patients and patients with multisystem atrophy-multineuron disease was determined. (Table 4) Tissue preparation and GDH determinations were done according to methods previously reported. [A. D. Colon, A. Plaitakis, S. Berl, and D. D. Clark. "The purification and characterization of soluble and particulate Glutamate Dehydrogenase in Rat Brain," *Neurochemistry*, 1986, 46:1811-1819. The contents of this publication are herein incorporated by reference] L-leucine produces a significant activation of GDH in tissue obtained from control cerebellum, and from tissue obtained from multisystem atrophy-multineuron degeneration disease cerebellum and frontal cortex. L-leucine concentrations as low as 0.15 mM are effective in producing increases in GDH activity and this effect is concentration dependent. The demonstration of leucine mediated activation of GDH at concentrations between 0.15 and 0.5 mM is important as plasma leucine levels of between about 0.45 to 0.30 mM at 1 and 2 hours, respectively, are obtained following administration of the amino acid composition to patients with ALS. FIG. 4.

TABLE 4

In Vitro Leucine Activation of
Membrane Bound GDH in Purified Brain

| | Percent Baseline GDH Activity | | |
| --- | --- | --- | --- |
| | Control | Mutisystem Atrophy Multineuron Disease | |
| Leucine Concentration (mM) | Patient Cerebellum | Patient 1 Cerebellum | Patient 2 Frontal Cortex |
| 0.0 | 100 | 100 | 100 |
| 0.15 | — | — | 122 |
| 0.25 | 117 | 117 | 128 |
| 0.50 | 135 | 153 | 141 |
| 1.0 | 143 | 186 | — |
| 2.5 | 155 | — | — |
| 5.0 | 155 | 176 | — |
| 10 | 160 | 176 | — |

The aforementioned articles are incorporated herein by reference.

While we have hereinbefore described a number of embodiments of this invention, it is apparent that the basic constructions can be altered to provide other embodiments which utilizes the treatments and compositions of this invention. Therefore, it will be appreciated that the scope of this invention is to be defined by the claims appended hereto rather than by the specific embodiments which have been presented hereinbefore by way of example.

We claim:

1. A method of treatment in mammals of the progressive exacerbation of symptoms associated with neurodegenerative disorders characterized by glutamate toxicity, not related to a decreased activity of glutamate dehydrogenase, but which is associated with abnormal glutamate metabolism, elevated levels of peripheral glutamate, or altered glutamate receptor characteristics wherein the treatment comprises administering to an individual in need of treatment a composition which is effective for treating one or more of said neurodegenerative disorders, and wherein the composition comprises at least one member of the group consisting of L-leucine, L-isoleucine and L-valine, wherein the amino acids are present in said composition in a proportion sufficient to maintain plasma levels of L-leucine, L-isoleucine, and L-valine at or above their untreated levels.

2. The treatment according to claim 1, wherein the mammals are humans, and the neurodegenerative disorders are selected from the group consisting of amyotrophic lateral sclerosis, Alzheimer's disease, Huntington's chorea, spinocerebellar degenerations, and other disorders characterized by degeneration of motor and other neurons of the central nervous system.

3. The treatment according to claim 1, wherein the amino acid composition is comprised of branched chain amino acids.

4. The treatment according to claim 3, wherein the composition of branched chain amino acids comprises L-leucine, L-isoleucine, and L-valine.

5. The treatment according to claim 4 wherein the the total daily dose of each of the amino acids is within a range of about:
   a. L-leucine, 0.3 to 30 grams;
   b. L-isoleucine, 0.2 to 20 grams;
   c. L-valine, 0.16 to 16 grams.

6. The treatment according to claim 5, wherein the total daily dose of each the amino acids is within a range of about:
   a. L-leucine, 12 to 18 grams;
   b. L-isoleucine, 8 to 12 grams;
   c. L-valine, 3.2 to 9.6 grams.

7. The treatment according to claim 5, wherein the total daily dose is divided so as to be administered four times per day.

8. The treatment according to claim 5, wherein the total daily dose is divided so as to be administered 6 times per day.

9. The treatment according to claim 1, wherein the total daily dose is administered to an individual in need of treatment, so as to maintain minimum effective therapeutic concentrations in plasma.

10. The treatment according to claim 5, wherein doses of amino acids are administered to an individual in need of treatment, orally or parenterally.

11. The treatment according to claim 4, wherein doses of the amino acids are of an amount sufficient to increase plasma levels of the amino acids above the untreated level, wherein the percent increase over untreated levels for each amino acid are within the ranges of about:
   a. L-leucine, 50 to 600 %;
   b. L-isoleucine, 40 to 500 %;
   c. L-valine, 25 to 300 %.

12. The treatment according to claim 4, wherein doses of the amino acids are of an amount sufficient to increase plasma levels of the amino acids above the untreated level, wherein the percent increase over untreated levels for each amino acid are within the ranges of about:
   a. L-leucine, 100 to 300 %;
   b. L-isoleucine, 80 to 250 %;
   c. L-valine, 50 to 150 %.

13. The treatment according to claim 12, wherein the neurodegenerative disorder is amyotrophic lateral sclerosis.

14. A pharmaceutical composition which is effective for treating neurodegenerative disorders wherein the composition comprises at least one amino acid selected from the group consisting of L-leucine, L-isoleucine and L-valine, wherein the amino acids are present in said composition in a proportion sufficient to maintain plasma levels or L-leucine, L-isoleucine and L-valine at or above their untreated levels with the proviso that when said composition comprises L-leucine, L-isoleucine and L-valine the ratio of L-leucine: L-isoleucine: L-valine in said composition is about 1.88–188:1.-25–125:1.

15. A method of treatment in mammals of the progressive exacerbation of symptoms associated with neurodegenerative disorders characterized by glutamate toxicity wherein the treatment comprises administering to an individual in need of treatment a composition which is effective for treating one or more of said neurodegenerative disorders, which composition comprises one or more amino acids which activate glutamate dehydrogenase, with the proviso that when said composition comprises the amino acids L-leucine, L-isoleucine and L-valine the ratio of L-leucine:L-isoleucine:L-valine present in said composition is 1:88–188:1.-25–125:1.

16. The treatment according to claim 15 wherein the mammals are humans, and the neurodegenerative disorders are selected from the group consisting of amyotrophic lateral sclerosis, Alzheimer's disease, Huntington's chorea, spinocerebellar degenerations, and other disorders characterized by degenerations of motor and other neurons of the central nervous system.

17. The treatment according to claim 15 wherein the amino acid composition is comprised of branched chain amino acids.

18. The treatment according to claim 17 wherein the composition of branched chain amino acids comprises L-leucine, L-isoleucine, and L-valine.

19. The treatment according to claim 18 wherein doses of the amino acids are of an amount sufficient to increase plasma levels of the amino acids above the untreated levels, wherein the percent increase over untreated levels for each amino acid is within the range of about 50% to 600% for L-leucine, 40% to 500% for L-isoleucine, and 25% to 300% for L-valine.

20. The treatment according to claim 18 wherein doses of the amino acids are of an amount sufficient to increase plasma levels of the amino acids above the untreated levels, wherein the percent increase over untreated levels for each amino acid is within the range of about 100% to 300% for L-leucine, 80% to 250% for L-isoleucine, and 50% to 150% for L-valine.

21. The treatment according to claim 20 wherein the neurodegenerative disorder is amyotrophic lateral sclerosis.

22. The pharmaceutical composition according to claim 14, wherein the mixture of amino acids comprises branched chain amino acids.

23. The pharmaceudical composition according to claim 22, wherein the mixture of amino acids comprises L-leucine, L-isoleucine, and L-valine.

24. The pharmaceutical composition according to claim 23, wherein the ratio of the amount of L-leucine:L-isoleucine:L-valine present in the composition is about 3.0:2.0:1.6.

* * * * *

UNITED STATES PATENT AND TRADEMARK OFFICE
CERTIFICATE OF CORRECTION

PATENT NO. : 5,028,622
DATED : July 2, 1991
INVENTOR(S) : Andreas Plaitakis

It is certified that error appears in the above-indentified patent and that said Letters Patent is hereby corrected as shown below:

Column 2, line 4, after "respectively", insert --,--;
         line 15, after "Disorders", insert --"--;
         line 67, delete "in vitro", insert --*in vitro*--.

Column 3, line 67, delete "pont", insert --point--;
         line 68, delete "set", insert --see--.

Column 4, line 50, before "1985", delete "10";
         line 58, delete "completey", insert --completely--.

Column 7, line 35, after "(CBC", insert --)--.
         line 44, delete "Platakis", insert --Plaitakis--.

Column 8, line 66, delete "THe", insert --The--.

Column 9, line 16, delete "ohi", insert --chi--;
         line 37, delete "a", insert --at--;
         line 57, delete "Neurologyl", insert --*Neurologyl*--.

Column 10, line 44, delete "in vitro", insert --*in vitro*--.

UNITED STATES PATENT AND TRADEMARK OFFICE
CERTIFICATE OF CORRECTION

PATENT NO. : 5,028,622
DATED : July 2, 1991
INVENTOR(S) : Andreas Plaitakis

It is certified that error appears in the above-indentified patent and that said Letters Patent is hereby corrected as shown below:

Column 11, line 2, delete "In Vitro", insert --*In Vitro*--;
line 67, after "each", insert --of--.

Column 12, line 45, delete "or", insert --of--.

Column 12, line 63, delete "1:88", insert --1.8--.

Column 14, line 11, delete "pharmaceudical", insert --pharmaceutical--.

Signed and Sealed this

Twenty-eighth Day of September, 1993

Attest:

BRUCE LEHMAN

*Attesting Officer*    *Commissioner of Patents and Trademarks*